United States Patent
Barrus

(10) Patent No.: US 9,452,000 B2
(45) Date of Patent: Sep. 27, 2016

(54) ROD REDUCER

(71) Applicant: K2M, Inc., Leesburg, VA (US)

(72) Inventor: Michael Barrus, Ashburn, VI (US)

(73) Assignee: K2M, Inc., Leesburg, VA (US)

( * ) Notice: Subject to any disclaimer, the term of this patent is extended or adjusted under 35 U.S.C. 154(b) by 21 days.

(21) Appl. No.: 14/508,180

(22) Filed: Oct. 7, 2014

(65) Prior Publication Data

US 2015/0100097 A1    Apr. 9, 2015

Related U.S. Application Data

(60) Provisional application No. 61/887,907, filed on Oct. 7, 2013.

(51) Int. Cl.
    *A61B 17/88*      (2006.01)
    *A61B 17/70*      (2006.01)
    *A61B 17/00*      (2006.01)

(52) U.S. Cl.
    CPC .. *A61B 17/7086* (2013.01); *A61B 2017/00424* (2013.01)

(58) Field of Classification Search
    CPC .......... A61B 17/7085; A61B 17/7086; A61B 17/7032; A61B 17/708; A61B 17/7002; A61B 17/7037; A61B 17/7091; A61B 17/7076; A61B 17/7082; A61B 17/7074
    USPC ................. 606/86 A, 99, 250–279
    See application file for complete search history.

(56) References Cited

U.S. PATENT DOCUMENTS

| | | |
|---|---|---|
| 2,248,054 A | 7/1941 | Becker |
| 3,604,487 A | 9/1971 | Gilbert |
| 4,263,899 A | 4/1981 | Burgin |
| 5,020,519 A | 6/1991 | Hayes et al. |
| 5,364,397 A | 11/1994 | Hayes et al. |
| 5,420,751 A | 5/1995 | Burns |
| 5,431,658 A | 7/1995 | Moskovich |
| 5,466,243 A | 11/1995 | Schmieding et al. |
| 5,529,571 A | 6/1996 | Daniel |
| 5,685,826 A | 11/1997 | Bonutti |
| 5,720,751 A | 2/1998 | Jackson |
| 5,910,141 A | 6/1999 | Morrison et al. |
| 5,944,658 A | 8/1999 | Koros et al. |
| 5,951,564 A | 9/1999 | Schroder et al. |
| 6,123,707 A | 9/2000 | Wagner |
| 6,200,322 B1 | 3/2001 | Branch et al. |
| 6,416,521 B1 | 7/2002 | Waldner et al. |
| 6,440,133 B1 | 8/2002 | Beale et al. |
| 6,488,682 B2 | 12/2002 | Kikuchi et al. |
| 6,616,605 B2 | 9/2003 | Wright et al. |

(Continued)

OTHER PUBLICATIONS

International Search Report and Written Opinion from Int'l Appl. No. PCT/US14/59425 mailed Jan. 12, 2015.

*Primary Examiner* — Mary Hoffman
*Assistant Examiner* — Tara R Carter
(74) *Attorney, Agent, or Firm* — Carter, DeLuca, Farrell & Schmidt, LLP

(57) ABSTRACT

A rod reducer apparatus is disclosed and includes a housing, an anvil coupled to a shaft, a plurality of arm members, and a button. The housing has an opening extending therethrough for receiving the shaft. The anvil is coupled to one end of the shaft. The button is slidably disposed in the housing and transitionable between first and second positions. The button is engageable with the shaft such that rotation of the shaft is translated into linear movement of the anvil.

18 Claims, 13 Drawing Sheets

(56) References Cited

U.S. PATENT DOCUMENTS

| | | |
|---|---|---|
| 6,648,888 B1 | 11/2003 | Shluzas |
| 6,660,006 B2 | 12/2003 | Markworth et al. |
| 6,743,231 B1 | 6/2004 | Gray et al. |
| 6,746,449 B2 | 6/2004 | Jones et al. |
| 6,790,208 B2 | 9/2004 | Oribe et al. |
| 6,790,209 B2 | 9/2004 | Beale et al. |
| 6,849,064 B2 | 2/2005 | Hamada |
| 6,923,814 B1 | 8/2005 | Hildebrand et al. |
| 6,929,606 B2 | 8/2005 | Ritland |
| 6,932,822 B2 | 8/2005 | Oribe et al. |
| 6,957,758 B2 | 10/2005 | Aranyi |
| 7,008,422 B2 | 3/2006 | Foley et al. |
| 7,011,660 B2 | 3/2006 | Sherman et al. |
| 7,083,621 B2 | 8/2006 | Shaolian et al. |
| 7,156,849 B2 | 1/2007 | Dunbar et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,226,453 B2 | 6/2007 | Chao et al. |
| 7,250,052 B2 | 7/2007 | Landry et al. |
| 7,371,239 B2 | 5/2008 | Dec et al. |
| 7,462,182 B2 | 12/2008 | Lim |
| 7,473,267 B2 | 1/2009 | Nguyen et al. |
| 7,481,813 B1 | 1/2009 | Purcell |
| 7,491,207 B2 | 2/2009 | Keyer et al. |
| 7,491,208 B2 | 2/2009 | Pond, Jr. et al. |
| 7,497,869 B2 | 3/2009 | Justis |
| 7,520,879 B2 | 4/2009 | Justis et al. |
| 7,547,318 B2 | 6/2009 | Birkmeyer et al. |
| 7,563,264 B2 | 7/2009 | Landry et al. |
| 7,572,264 B2 | 8/2009 | Null et al. |
| 7,575,581 B2 | 8/2009 | Lovell |
| 7,588,575 B2 | 9/2009 | Colleran et al. |
| 7,588,588 B2 | 9/2009 | Spitler et al. |
| 7,591,836 B2 | 9/2009 | Dick et al. |
| 7,608,081 B2 | 10/2009 | Abdelgany |
| 7,611,517 B2 | 11/2009 | Lim |
| 7,618,442 B2 | 11/2009 | Spitler et al. |
| 7,621,918 B2 | 11/2009 | Jackson |
| 7,625,379 B2 | 12/2009 | Puno et al. |
| 7,637,914 B2 | 12/2009 | Stern |
| 7,651,502 B2 | 1/2010 | Jackson |
| 7,655,008 B2 | 2/2010 | Lenke et al. |
| 7,666,189 B2 | 2/2010 | Gerber et al. |
| 7,691,132 B2 | 4/2010 | Landry et al. |
| 7,708,763 B2 | 5/2010 | Selover et al. |
| 7,776,040 B2 | 8/2010 | Markworth et al. |
| 7,854,751 B2 | 12/2010 | Sicvol et al. |
| 7,887,541 B2 | 2/2011 | Runco et al. |
| 7,909,835 B2 | 3/2011 | Oribe et al. |
| 7,922,749 B2 | 4/2011 | Dewey |
| 7,927,334 B2 | 4/2011 | Miller et al. |
| 7,946,982 B2 | 5/2011 | Hamada |
| 7,955,355 B2 | 6/2011 | Chin |
| 7,988,694 B2 | 8/2011 | Barrus et al. |
| 8,002,798 B2 | 8/2011 | Chin et al. |
| 8,147,524 B2 | 4/2012 | Piza Vallespir |
| 8,192,438 B2 | 6/2012 | Garamszegi |
| 8,230,863 B2 | 7/2012 | Ravikumar et al. |
| 8,298,138 B2 | 10/2012 | Gorek et al. |
| 8,303,595 B2 | 11/2012 | Jones |
| 8,308,729 B2 | 11/2012 | Nunley et al. |
| 2002/0052603 A1 | 5/2002 | Nichols et al. |
| 2003/0225408 A1 | 12/2003 | Nichols et al. |
| 2004/0215190 A1 | 10/2004 | Nguyen et al. |
| 2004/0230191 A1 | 11/2004 | Frey et al. |
| 2004/0267275 A1 | 12/2004 | Cournoyer et al. |
| 2005/0059969 A1* | 3/2005 | McKinley ......... A61B 17/7086 606/86 A |
| 2005/0143749 A1 | 6/2005 | Zalenski et al. |
| 2005/0149053 A1 | 7/2005 | Varieur et al. |
| 2005/0192587 A1 | 9/2005 | Lim |
| 2005/0192589 A1 | 9/2005 | Raymond et al. |
| 2005/0261702 A1 | 11/2005 | Oribe et al. |
| 2005/0277934 A1* | 12/2005 | Vardiman .......... A61B 17/7083 606/914 |
| 2006/0025769 A1 | 2/2006 | Dick et al. |
| 2006/0036260 A1 | 2/2006 | Runco et al. |
| 2006/0074418 A1 | 4/2006 | Jackson |
| 2006/0089651 A1 | 4/2006 | Trudeau et al. |
| 2006/0200132 A1 | 9/2006 | Chao et al. |
| 2006/0271050 A1 | 11/2006 | Piza Vallespir |
| 2007/0016193 A1* | 1/2007 | Ritland .............. A61B 17/7011 606/257 |
| 2007/0055247 A1 | 3/2007 | Jahng |
| 2007/0093817 A1 | 4/2007 | Barrus et al. |
| 2007/0213716 A1 | 9/2007 | Lenke et al. |
| 2007/0213722 A1 | 9/2007 | Jones et al. |
| 2007/0270811 A1 | 11/2007 | Dewey |
| 2007/0270867 A1 | 11/2007 | Miller et al. |
| 2007/0276379 A1* | 11/2007 | Miller ................ A61B 17/7088 606/86 A |
| 2007/0282337 A1 | 12/2007 | Garamszegi |
| 2008/0015601 A1 | 1/2008 | Castro et al. |
| 2008/0172062 A1 | 7/2008 | Donahue et al. |
| 2009/0018593 A1 | 1/2009 | Barrus et al. |
| 2011/0054259 A1 | 3/2011 | Gorek et al. |
| 2011/0118791 A1* | 5/2011 | Nunley et al. ..... A61B 17/7086 606/279 |
| 2011/0172714 A1 | 7/2011 | Boachie-Adjei et al. |
| 2012/0083853 A1 | 4/2012 | Boachie-Adjei et al. |
| 2013/0041228 A1 | 2/2013 | Gorek et al. |
| 2013/0046344 A1 | 2/2013 | Nunley et al. |

* cited by examiner

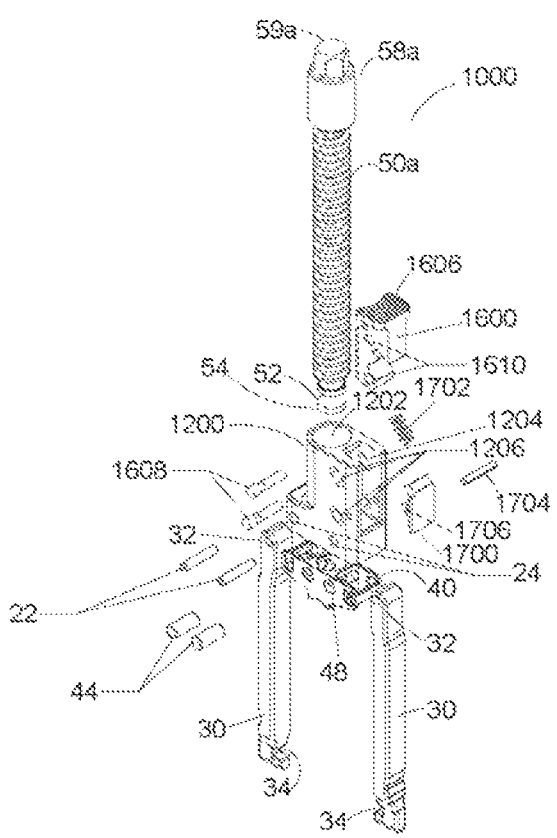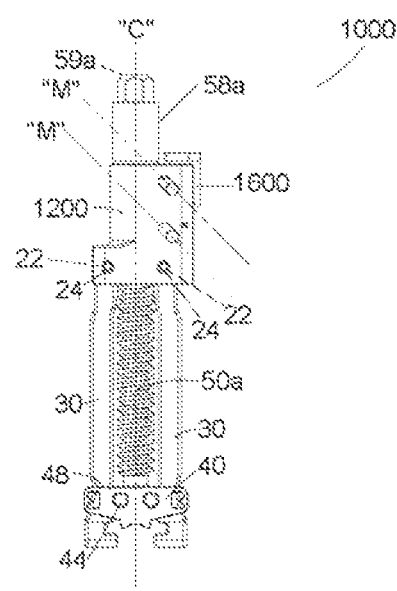
FIG. 11
FIG. 10

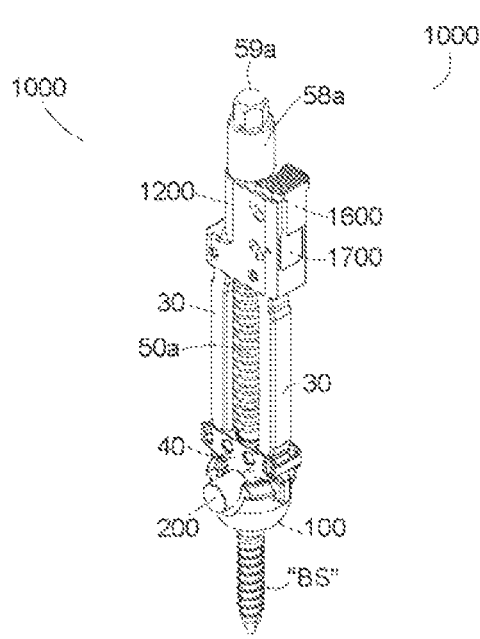
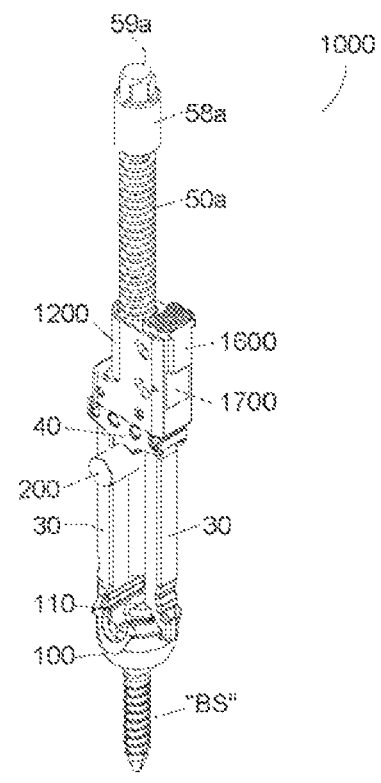
FIG. 15B
FIG. 15A

ROD REDUCER

CROSS-REFERENCE TO RELATED APPLICATIONS

The present application claims the benefit of U.S. Provisional Application Ser. No. 61/887,907, which was filed on Oct. 7, 2013, the entire contents of which are incorporated herein by reference.

BACKGROUND

1. Technical Field

The present disclosure relates to orthopedic surgery apparatus for stabilizing and fixing the bones and joints of the body. Particularly, the present disclosure relates to a manually operated apparatus for reducing a spinal rod into a bone screw in a controlled, measured, and efficient manner.

2. Description of Related Art

The spinal column is a complex system of bones and connective tissues that provides support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending, and rotational loads and motions.

There are various disorders, diseases, and types of injury that the spinal column may experience in a lifetime. The problems may include but are not limited to scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to stabilize or eliminate motion at the intervertebral disc or joint. To achieve this, natural or artificial bone, along with a spacing device, replaces either part, or all of the intervertebral disc to form a rigid column of bone, which is stabilized by mechanical hardware.

The mechanical hardware used to immobilize the spinal column typically involves a series of bone screws/anchors and metal rods or plates. When the spine surgery is performed posteriorly, it is common practice to place bone screws into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of a bone screws and then securing that connecting rod in place can often require that the clinician use a number of instruments and expend a great deal of time and effort. When bone screws in several adjacent vertebrae are to be securely connected by a spinal rod, the repeated process of inserting the rod into the screw housing of the bone screws and then securing the rod in place for each respective bone screw can be difficult, tiresome, and time consuming. Further, the alignment of the rod as it connects to each of the sequential bone screws may require adjustment during the procedure and, therefore it is desirable that an apparatus and method be provided by which the rod can be reduced into the screw housing of each of the sequentially aligned bone screws and, as necessary, easily adjusted so as to facilitate the process for the clinician with minimal effort and loss of time. Therefore, a need exits for an efficient way to reduce the rod into the screw housing and lock the rod in place.

SUMMARY

The present disclosure is directed to a rod reducer apparatus including a housing having an opening, a shaft disposed through the opening, the shaft having threads formed thereon, an anvil coupled to the shaft, a button slidably disposed in the housing and transitionable between a first position wherein the threads of the shaft are engaged with threads on the button and a second position wherein the threads of the shaft are spaced apart from the threads on the button, the button biased towards the first position, and first and second arm members operatively coupled to the housing and configured to engage a bone screw, wherein rotation of the shaft with the button in the first position translates into linear movement of the shaft relative to the housing and linear movement of the shaft with the button in the second position is independent of shaft rotation.

In one embodiment, the rod reduction apparatus further includes a spring element for biasing the button towards the first position.

In one embodiment, the first and second arms are repositionable towards a parallel configuration as the anvil is moved away from the housing.

In a further embodiment, the shaft cooperatively engages threads of the button with the button in the first position.

In yet another embodiment, the first and second arm members are pivotably coupled to the housing.

In a further embodiment, the first and second arm members are flexibly coupled to the housing.

In one embodiment, a first surface of the button includes the threads.

In yet another embodiment, the first surface of the button transitions away from a longitudinal axis of the housing when in the second position.

In an aspect of the present disclosure, the button has an ergonomic grip feature disposed on a second surface.

In another embodiment, the rod reducer apparatus includes a receiving saddle disposed on the anvil, such that the receiving saddle cooperatively engages with a surface of a spinal rod.

In an embodiment, the receiving saddle is generally formed into an arch, and is adapted to engage a variety of spinal rod diameters.

In another aspect of the present disclosure, a method for reducing a spinal rod into a bone screw includes providing a rod reducer apparatus, the rod reducer apparatus including a housing having an opening, a shaft disposed through the opening, the shaft having threads formed thereon, an anvil coupled to the shaft, a button slidably disposed in the housing and transitionable between a first position wherein the threads of the shaft are engaged with threads on a first surface of the button and a second position wherein the threads of the shaft are spaced apart from the first surface, and first and second arm members operatively coupled to the housing and configured to engage a bone screw, the first and second arms movable towards a parallel configuration as the anvil is advanced away from the housing, wherein rotation of the shaft with the button in the first position translates into linear movement of the shaft relative to the housing and linear movement of the shaft with the button in the second position is independent of shaft rotation. The method also includes coupling the rod reducer apparatus with the bone screw, positioning the spinal rod between the anvil and the screw housing of the bone screw, transitioning the button of the rod reducer apparatus into the second position, sliding the shaft distally such that the first and second arm members grasp the bone screw, and engaging the spinal rod with the anvil.

In one embodiment of the present disclosure, the method may further include, transitioning the button of the rod reducer apparatus to the first position and rotating the shaft such that the anvil travels linearly with respect to the housing towards the spinal rod to urge the spinal rod into engagement with the screw housing of the bone screw.

In yet another embodiment of the present disclosure, the method may further include transitioning the button of the rod reducer apparatus to the second position and sliding the anvil away from the spinal rod.

In a further embodiment of the present disclosure, the method includes translating the anvil proximally into a proximal most position and decoupling the first and second arm members of the rod reducer apparatus from the bone screw.

In a further embodiment of the present disclosure, the method includes positioning the shaft, and anvil attached thereto, into a proximal most position, and decoupling the arm members of the rod reducer apparatus from the bone screw.

In yet another embodiment of the present disclosure, the method may further include selecting the spinal rod from a plurality of spinal rods having varying diameters, selecting the bone screw from a plurality of bone screws having a variety of sizes, and reducing the selected spinal rod into the selected bone screw.

In yet another embodiment of the present disclosure, the method may further include implanting at least one bone screw into a bone of a subject.

In another aspect of the present disclosure, a kit is provided. The kit includes a rod reducer apparatus, a plurality of bone screws, and a spinal rod. The at least one rod reducer apparatus includes, a housing, a shaft and an anvil operably associated with the housing, a button slidably disposed in the housing and transitionable between a first position and a second position, and first and second arm members coupled to the housing and configured to engage a bone screw, the first and second arms movable towards a parallel configuration in response to movement of the anvil relative to the housing, wherein rotation of the shaft with the button in the first position translates into linear movement of the shaft relative to the housing and linear movement of the shaft with the button in the second position is independent of shaft rotation.

BRIEF DESCRIPTION OF THE DRAWINGS

The above and other aspects and features of the present disclosure will become more apparent in light of the following detailed description when taken in conjunction with the accompanying drawings in which:

FIG. 10 is a front view of a second embodiment of a rod reducer apparatus in accordance with the present disclosure;

FIG. 11 is an perspective view, with parts separated, of the rod reducer apparatus of FIG. 10;

FIG. 15A is a perspective view of the rod reducer apparatus of FIG. 10 coupled to a bone screw prior to reducing a rod; and FIG. 15B is a perspective view of the rod reducer apparatus of FIG. 15A after reducing the rod into the bone screw.

DETAILED DESCRIPTION OF EMBODIMENTS

Figure 3:
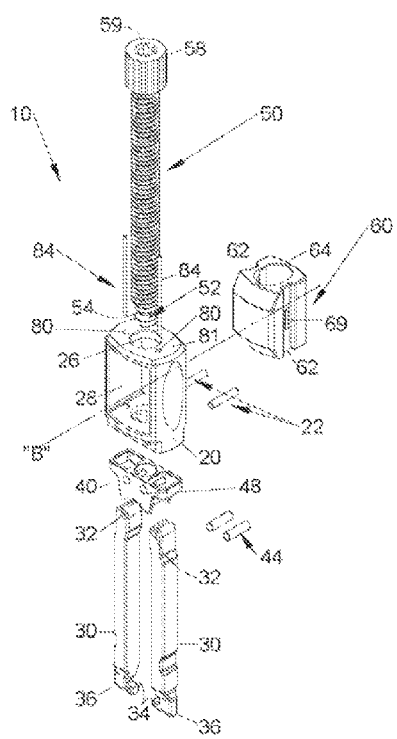
FIG. 3 is an perspective view, with parts separated, of the rod reducer apparatus of FIGS. 1 and 2.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the apparatus or component thereof that is closer to the clinician and the term "distal" will refer to the portion of the apparatus or component thereof that is farther from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient, whereas "medial" refers to a position toward the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 2:
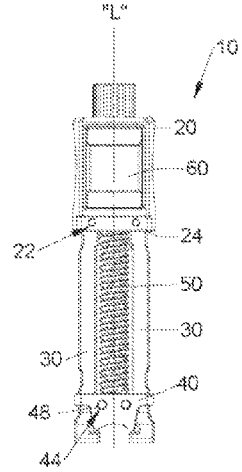
FIG. 2 is a front view of the rod reducer apparatus of FIG. 1 in a second orientation.
Figure 1:
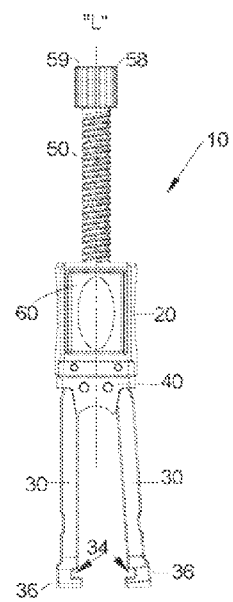
FIG. 1 is a front view of one embodiment of a rod reducer apparatus, in a first orientation, in accordance with the present disclosure.
Figure 4A:
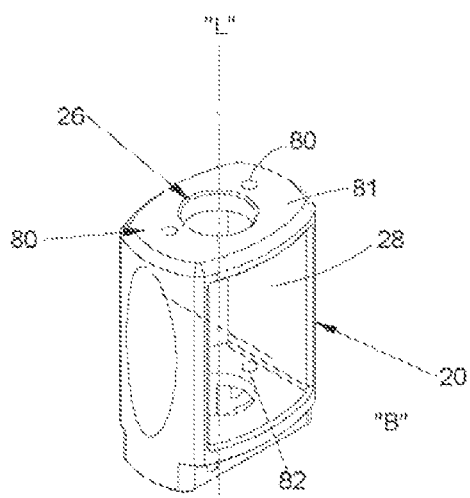
FIG. 4A is a front perspective view of one embodiment of a housing of the rod reducer apparatus of FIG. 1 in accordance with the present disclosure.
Figure 4B:
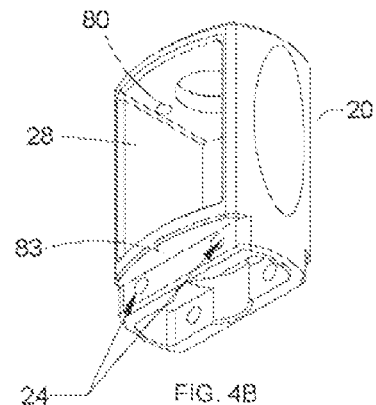
FIG. 4B is a rear perspective view of the housing of FIG. 4A.
Figure 6:
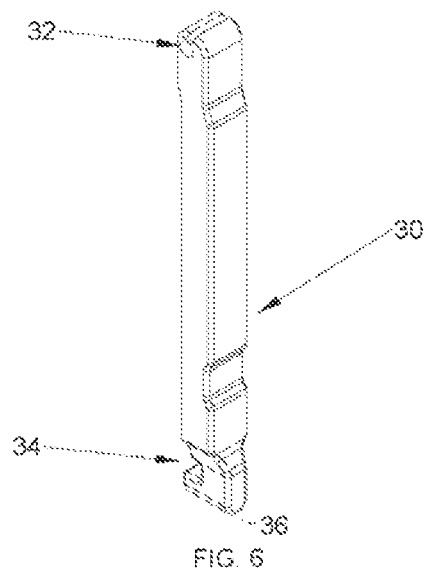
FIG. 6 is a perspective view of an arm member of a rod reducer apparatus in accordance with the present disclosure.
Figure 7:
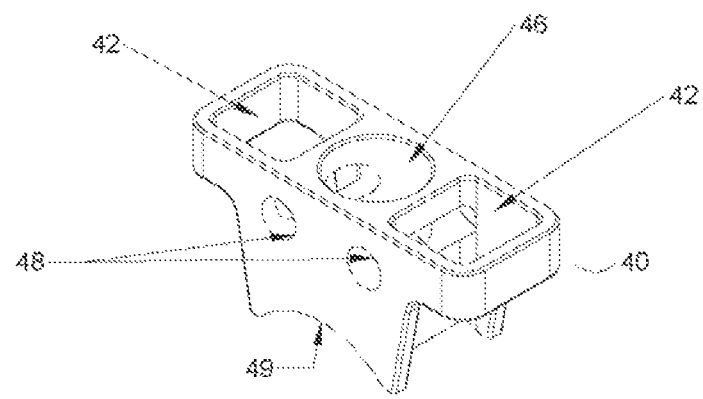
FIG. 7 is a perspective view of an anvil of a rod reducer apparatus in accordance with the present disclosure.
Figure 8:
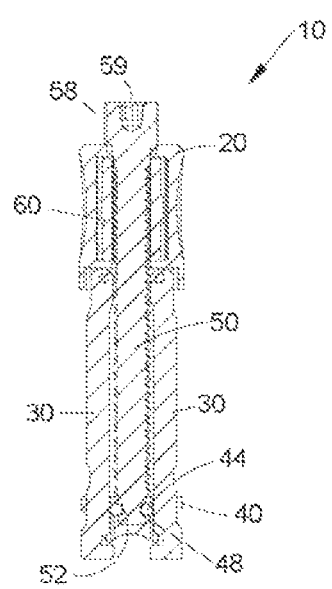
FIG. 8 is a side cross-sectional view of the rod reducer apparatus of FIG. 2 in accordance with the present disclosure.
Figure 9B:
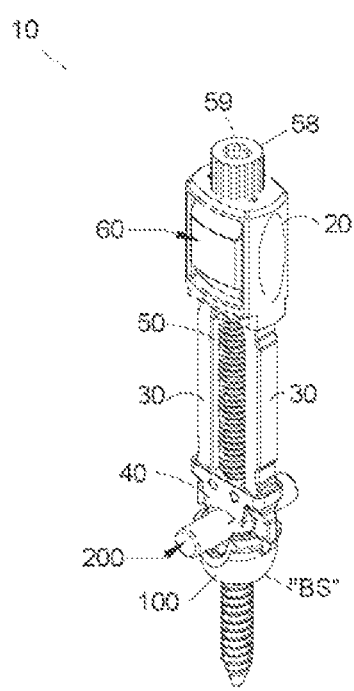
FIG. 9B is a perspective view of the rod reducer apparatus of FIG. 9A after reducing the rod into the bone screw.
Figure 9A:
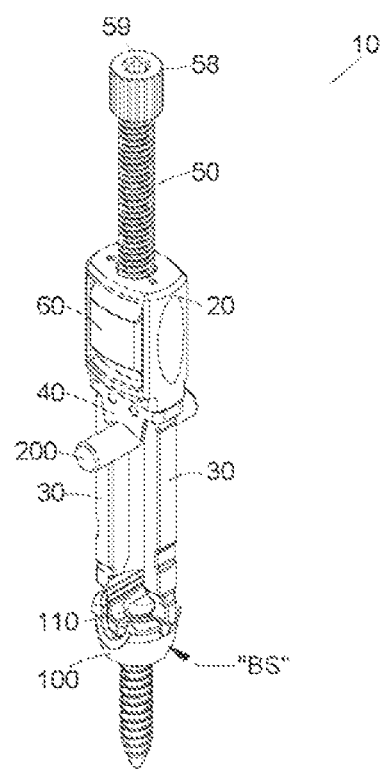
FIG. 9A is a perspective view of the rod reducer apparatus of FIG. 1 coupled to a bone screw prior to reducing a rod.
Figure 10A:
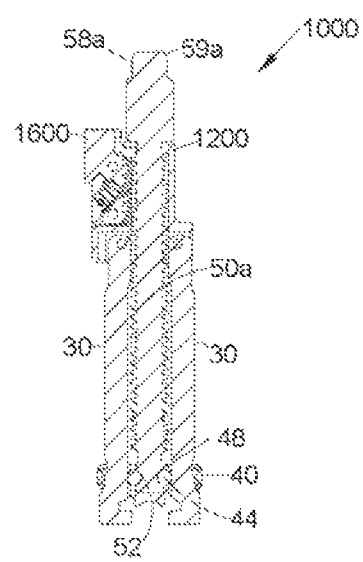
FIG. 10A is a side cross-sectional view of the rod reducer apparatus of FIG. 10.

Referring initially to FIGS. 1-3, a rod reducer apparatus in accordance with the present disclosure is generally designated as 10. Rod reducer apparatus 10 includes a housing 20, a plurality of arm members 30, an anvil 40 coupled to a shaft 50, and a button 60. With further reference to FIGS. 4A, 4B and 7, rod reducer apparatus 10 may include two arm members 30. Each arm member 30 is insertable through a respective cavity 42 of the anvil 40. In one embodiment as shown, arm members 30 are pinned in place relative to housing 20 with pins 22. Alternatively, it is contemplated that arm members 30 may be integrally formed with housing 20 such that, rather than pivoting relative to housing 20, arm members 30 flex relative to housing 20. In such an embodiment, pins 22 may be omitted and arms 30 may be directly attached to housing 20. Pins 22 extend through a respective pin hole 24 of the housing 20 and a respective pin hole 32 (as seen in FIG. 6) of each arm member 30. Pin holes 32 in combination with pins 22 and pin holes 24 define a pivot axis for first and second arm members 30. As seen in FIG. 6, each arm member 30 has a hook portion 34 at its distal end 36 for engaging a screw housing 100 that is disposed at a proximal end of a bone screw "BS" (as seen in FIGS. 9A and 9B). During reduction of a spinal rod 200 (FIG. 9B), arm members 30 move towards a parallel configuration, such that hook portion 34 of each respective arm member 30 may engage bone screw "BS" (as seen in FIGS. 9A and 9B). Engagement of hook portion 34 to bone screw "BS" serves to maintain alignment of rod reducer apparatus 10 with respect to the screw housing 100 as spinal rod 200 is reduced into the screw housing 100.

With reference to FIGS. 1 and 2, anvil 40 and arm members 30 will be further described. Proximal and distal translation of anvil 40 causes each arm member 30 to pivot with respect to housing 20 about their respective pin holes 32. In an alternate embodiment, each arm member 30 flexes relative to housing 20 as anvil 40 is translated proximally and distally with respect to housing 20. As seen in FIG. 1, with anvil 40 in a proximal most position, arm members 30 are in a first position, and may be engaged or disengaged from screw housing 100 of bone screw "BS". As seen in FIG. 2, with anvil 40 in a distal most position, arm members 30 are in a second position, and are configured to be securely engaged with the screw housing 100 of bone screw "BS" (FIG. 9B). As anvil 40 travels distally with respect to housing 20 from the proximal most position to the distal most position, arm members 30 move from the first position towards a parallel configuration ending in the second position. As arm members 30 move towards a parallel configuration, hook portion 34 of each respective arm member 30 acts to engage the screw housing 100 of bone screw "BS" (as discussed above and seen in FIGS. 9A and 9B).

With reference to FIGS. 3, 7, 8, and 10A, the coupling of anvil 40 to shaft 50 will be described. Shaft 50 has threads thereon and includes a distal portion 54 with an annular groove 52, and a head 58 with a recess 59. It is envisioned that recess 59 may be configured to cooperatively engage with any number of counterpart drive tools known in the art to effect torque driven rotation. For example, recess 59 may be configured as a hex socket (as shown in FIG. 3), a hex head 59a (as shown in FIG. 11), a Philips head, or slotted head. Shaft 50 is insertable through aperture 46 of anvil 40. Pins 44 are used to maintain the shaft 50 within the anvil 40 by inserting pins 44 through pin holes 48 of anvil 40 such that a portion of each pin 44 resides in the annular groove 52 at the distal end 54 of shaft 50.

Figure 5:
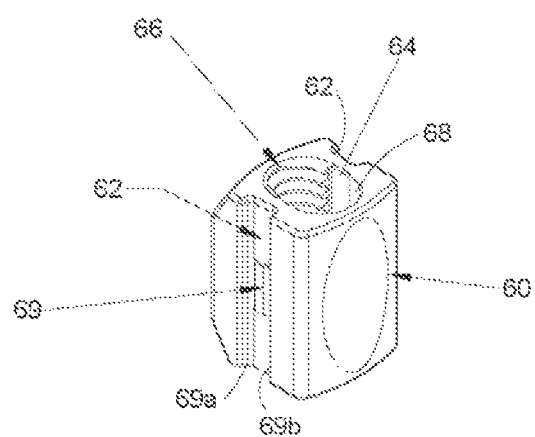
FIG. 5 a perspective view of one embodiment of a button of the rod reducer apparatus of FIG. 1 in accordance with the present disclosure.

With reference to FIGS. 1-5, the housing 20 and button 60 will be further described. Housing 20 of rod reducer apparatus 10 includes an opening 26. In one embodiment of the present disclosure, housing 20 defines a longitudinal axis "L" (as seen in FIGS. 1, 2, and 4A) such that opening 26 coincides with longitudinal axis "L". Housing 20 further includes a button cavity 28 disposed therein configured to receive button 60. Button 60 may have an elongated throughhole 64 extending therethrough (as seen in FIG. 5) which is alignable with the opening 26 of housing 20 such that shaft 50 is insertable therethrough. Housing 20 additionally has pin holes 80 on a top surface 81 and corresponding pin holes 82 (only one pin hole 82 is shown with the other pin hole being identical) on a bottom surface 83. Alignment pins 84 (as shown in FIG. 3) extend through pin holes 80 and into pin holes 82 respectively. It is envisioned that alignment pins 84 are positioned in grooves 62 which are disposed on opposing sides of button 60 (as seen in FIGS. 3 and 5). Each groove 62 of button 60 contains a boss 69 disposed thereon, which is utilized as a detent for the placement of button 60 in one of a first or second position. The position of button 60 is controlled by placement of the alignment pins 84 within the grooves 62, such that alignment pins 84 are disposed on a first side 69a of bosses 69 or on a second side 69b of bosses 69. It is envisioned that alignment pins 84 additionally aid button 60 to remain within housing 20 during actuation of rod reducer apparatus 10. It is further envisioned that button 60 may be held in place within button cavity 28 by the shaft 50 passing through the opening 26 of housing 20 and the elongated throughhole 64 of button 60. Additionally, it is envisioned that elongated throughhole 64 has a diameter which is larger than a diameter of shaft 50.

With continued reference to FIGS. 3 and 5, engagement and disengagement of button 60 to shaft 50 will be described. In one embodiment of the present disclosure, an inner surface of the elongated throughhole 64 has a partially threaded portion 66 disposed thereon configured to receive shaft 50. The inner surface of the elongated throughhole 64 also has an unthreaded portion 68, opposite to threaded portion 66, to permit shaft 50 to slide freely therethrough. It is further envisioned that the elongated throughhole 64 may not be perfectly round, but may have an elongated or oval configuration, such that movement of the button 60 along axis "B" (as shown in FIGS. 3 and 4A) within the button cavity 28 of housing 20 moves the threaded portion 66 of button 60 into and out of engagement with shaft 50.

As discussed above, button 60 is in the first position when alignment pins 84 are on the first side 69a of bosses 69, and button 60 is in the second position when alignment pins 84 are on the second side 69b of bosses 69. It will be appreciated that bosses 69, within channels 62 act to maintain button 60 into one of either the first or second positions during articulation of rod reducer apparatus 10. Once button 60 is transitioned from the first position to the second position, button 60 remains in the second position until it is manually transitioned back to the first position. To transition button 60 from the first position to the second position, button 60 is moved along axis "B" with respect to housing 20 and relative to alignment pins 84 such that alignment pins 84 disengage from the first side 69a of the bosses 69 and engage the second side 69b of the bosses. To transition button 60 from the second position to the first position, the same process is completed in reverse.

With button 60 in the first position, threaded portion 66 of button 60 is coupled to the shaft 50, permitting torque driven rotation and proximal and distal translation of the shaft 50 within the opening 26 (as seen in FIG. 4A) of the housing 20. In the second position, threaded portion 66 of button 60 is uncoupled from shaft 50 permitting free movement of the shaft 50 within the opening 26 of the housing 20. It is envisioned that unthreaded portion 68 of the button 60 may be in near abutment to shaft 50 in the second position. In other words, with threaded portion 66 engaged to shaft 50, proximal and distal movement of shaft 50 and anvil 40 is directly proportional to the threaded configuration of the shaft 50 and the threaded portion 66, and may be thought of as a fine adjustment during reduction of a spinal rod. Further, with threaded portion 66 disengaged from shaft 50, proximal and distal movement of shaft 50 is not constrained allowing rapid movement of the shaft 50 and anvil 40 relative to the housing 20, and may be thought of as a course adjustment during reduction of a spinal rod.

With reference to FIGS. 9A and 9B, the movement of the shaft 50 and anvil 40 will be further discussed with respect to the engagement and disengagement of the button 60. During engagement of button 60 and torque driven rotation of shaft 50, anvil 40 may travel towards and away from housing 20 in unison with the proximal and distal translation of shaft 50. During reduction of spinal rod 200 into bone screw "BS", threaded rod 50 is manually rotated distally such that anvil 40 simultaneously travels distally with respect to housing 20 into contact with spinal rod 200 to urge spinal rod 200 into screw housing 100 such that spinal rod 200 is securely coupled to screw housing 100. With button 60 in the second position, threaded rod 50 can slide freely both proximally and distally within opening 26 of housing 20 causing anvil 40 to simultaneously move freely with respect to housing 20 in the proximal and distal directions.

With added reference to FIG. 7, anvil 40 and spinal rod 200 will be further described. During reduction of spinal rod 200, receiving saddle 49 of anvil 40 is in abutment to an outer surface (not shown) of spinal rod 200. It is envisioned that receiving saddle 49 is configured to accommodate a range of spinal rod diameters. For example, receiving saddle 49 may be adapted to cooperatively engage with a spinal rod 200 having a variance in diameter of between about 3 mm to about 8 mm, while still achieving the necessary driving force to secure the spinal rod 200 into a bone screw "BS". Receiving saddle 49 may be generally arched or convex, but may take the form of any geometric shape adapted to cooperatively engage with and drive a spinal rod during reduction.

An alternate embodiment of a rod reducer apparatus in accordance with the present disclosure will now be described with reference to FIGS. 10-15B, and is generally designated as 1000. Referring initially to FIGS. 10 and 11, rod reducer apparatus 1000 includes a housing 1200, arm members 30, anvil 40, shaft 50a, a button 1600, and a spring seat 1700. It should be appreciated that arm members 30 and anvil 40 are the same as discussed above, and for conciseness, will be omitted in discussion of rod reducer apparatus 1000. Shaft 50a replaces shaft 50 of the embodiment shown in FIG. 1. Shaft 50a differs from shaft 50 in that head 58a may have a generally smooth outer surface in comparison to the knurled outer surface of head 58 and recess 59 may be replaced with a hexagonal nut 59a for engaging an appropriate driving tool (not shown).

Figure 12:
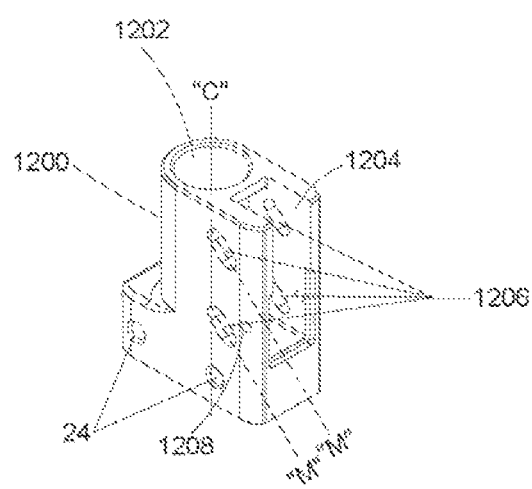
FIG. 12 is a front perspective view of one embodiment of a housing of the rod reducer apparatus of FIG. 10 in accordance with the present disclosure.
Figure 13B:
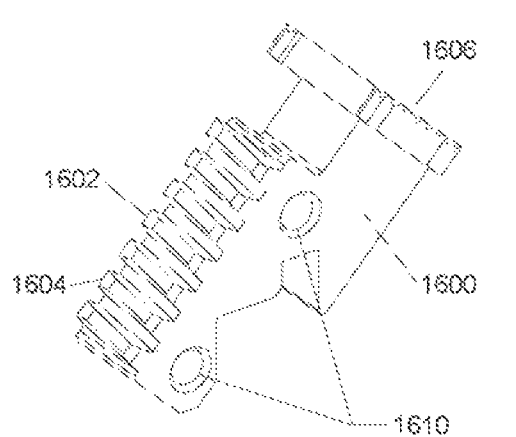
FIG. 13B is a rear perspective view of the button of FIG. 13A.
Figure 13A:
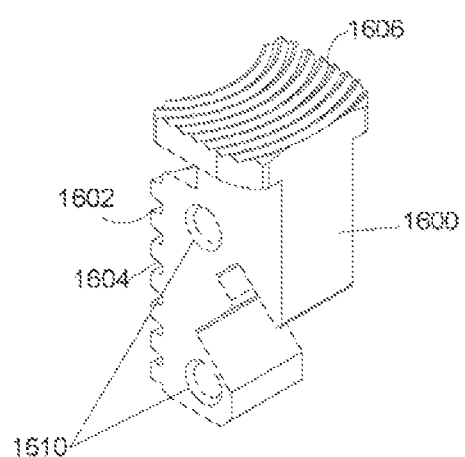
FIG. 13A a front perspective view of one embodiment of a button of the rod reducer apparatus of FIG. 10 in accordance with the present disclosure.
Figure 14B:
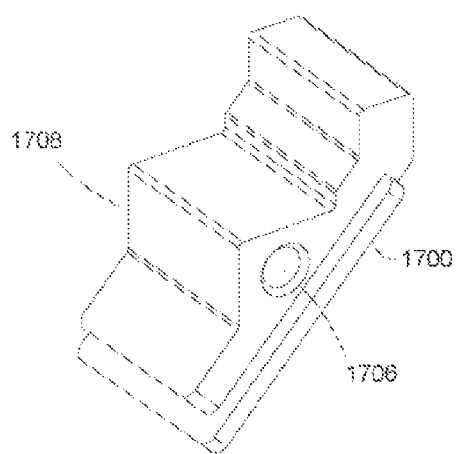
FIG. 14B is a rear perspective view of the spring seat of FIG. 14A.
Figure 14A:
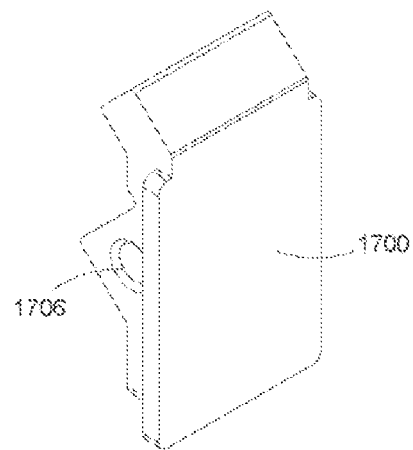
FIG. 14A is a front perspective view of a spring seat of the rod reducer apparatus of FIG. 10 in accordance with the present disclosure.

With reference to FIG. 12, housing 1200 of rod reducer apparatus 1000 will be further discussed. Housing 1200 includes an opening 1202. In one embodiment of the present disclosure, housing 1200 defines a longitudinal axis "C" (as seen in FIGS. 10 and 12) such that opening 26 is coaxially disposed about longitudinal axis "C". Housing 1200 further includes a button cavity 1204 disposed therein configured to receive button 1600. Button 1600 has a first surface 1602 (as seen in FIGS. 13A and 13B) which is alignable with the opening 1202 of housing 1200 such that shaft 50a may abut the first surface 1602 of button 1600. Further, the first surface 1602 of button 1600 may have a threaded portion 1604 disposed thereon configured to cooperatively engage with the threads disposed on shaft 50a. Button 1600 may further have a second surface 1606, such that an ergonomic grip feature is disposed thereon. Button 1600 is coupled to housing 1200 with pins 1608 (as shown in FIG. 11). Each pin 1608 extends through a slot 1206 of the housing 1200 and pin holes 1610 of button 1600. Slot 1206 of the housing is adapted to allow translation of button 1600 into and out of engagement with shaft 50a. More specifically, button 1600 is permitted to translate from a first position, wherein the first surface 1602 of button 1600 is in engagement to shaft 50a, into a second position, wherein the first surface 1602 is spaced apart from shaft 50a. It is envisioned that slot 1206 may be angled diagonally away from the longitudinal axis "C" of housing 1200. In one embodiment, each pin 1608 moves within slot 1206 along axis "M" (as seen in FIG. 12). Axis "M" intersects axis "C" such that an acute angle is defined therebetween. It is further envisioned, that slot 1206 may take any shape which permits button 1600 to translate from the first position to the second position, such as for example, an arcuate path. Each pin 1608 additionally aids button 1600 to remain within housing 1200 during actuation of rod reducer apparatus 1000.

As illustrated in FIG. 11, a spring 1702 may be disposed between button 1600 and a spring seat 1700 (seen in FIGS. 14A and 14B) in housing 1200. Spring 1702, button 1600, and spring seat 1700 are inserted into button cavity 1204 of housing 1200. Spring seat 1700 is held in place relative to housing 1200 with pin 1704. Pin 1704 extends through pin hole 1208 of the housing 1200 and pin hole 1706 of spring seat 1700. Spring seat 1700 further includes a spring surface 1708, contoured to receive spring 1700. Spring 1702 provides a biasing force that urges button 1600 towards the first position, keeping the threaded portion 1604 of button 1600 coupled to the shaft 50a. In a contemplated alternative, spring 1700 provides a biasing force which urges button 1600 into the second position, keeping the threaded portion 1604 of button 1600 uncoupled from the shaft 50a. In either embodiment, the biasing force of spring 1702 may be overcome to achieve the desired position of button 1600, allowing either manual rotation of shaft 50a within opening 1202 of housing 1200 in the first position, or conversely, allowing shaft 50a to freely slide within the opening 1202 of housing 1200 in the second position.

As similarly described above with respect to rod reducer apparatus 10, with respect to rod reducer apparatus 1000, the threaded portion 1604 of button 1600 is coupled to the shaft 50a in the first position, permitting torque driven rotation and proximal and distal translation of the shaft 50a within the opening 1202 (as seen in FIGS. 15A and 15B) of the housing 1200. In the second position, threaded portion 1604 of button 1600 is uncoupled from shaft 50a permitting free movement of the shaft 50a within the opening 1202 of the housing 1200. In other words, with threaded portion 1604 engaged to shaft 50a, proximal and distal movement of shaft 50a and anvil 40 is directly proportional to the threaded configuration of the shaft 50a and the threaded portion 1604, and may be thought of as a fine adjustment during reduction of a spinal rod. Further, with threaded portion 1604 disengaged from shaft 50a, proximal and distal movement of shaft 50a is not constrained allowing rapid movement of the shaft 50a and anvil 40 relative to the housing 1200, and may be thought of as a course adjustment during reduction of a spinal rod.

Operating a rod reduction apparatus in accordance with the present disclosure will be described with reference to FIGS. 1-15B. It should be appreciated that the method described below may be performed with rod reducer apparatus 10 in the same fashion as with rod reducer apparatus 1000. Specifically, button 60 of rod reducer apparatus 10 and button 1600 of rod reducer apparatus 1000 interact similarly within respect to the engagement and disengagement with shaft 50 and shaft 50a, respectively, as such, the method described below will be described with reference to rod reducer apparatus 10 for briefness. Differences between operation of rod reducer apparatus 10 and rod reducer apparatus 1000 will be pointed out as necessary.

A spinal rod and screw construct is assembled in a patient as follows. A clinician implants a bone screw "BS" into a spinal vertebra with a screw housings 100 of the bone screw "BS" positioned to receive a spinal rod 200 in a rod retaining seat or saddle portion 110 of the screw housing 100. It is envisioned that a clinician may implant multiple bone screws "BS" into several vertebrae during a procedure. Once the desired number of bone screws "BS" have been implanted, the clinician aligns and manipulates the spinal rod 200 such that a portion of the spinal rod 200 is in proximal relation to the screw housing 100 of each respective bone screw "BS", such that spinal rod 200 creates an unbroken connection between each bone screw "BS".

The clinician next positions a rod reducer apparatus 10, 1000 into proximity with each respective bone screw "BS", such that a hook portion 34 of arm members 30 of rod reducer apparatus 10 is in near abutment to the screw housing 100 of each respective bone screw "BS". Next, the clinician causes the hook portion 34 of the arm members 30 to grasp, clip, or otherwise affix to the screw housing 100, such that during reduction of spinal rod 200 attachment of rod reducer apparatus 10 to the bone screw "BS", and alignment of spinal rod 200 to the screw housing 100, is maintained. During reduction, spinal rod 200 is positioned between the screw housing 100, the anvil 40, and the arm members 30, and may be in abutment to the anvil 40 (as seen in FIGS. 9A and 15A) or in abutment to the screw housing 100 (as seen in FIGS. 9B and 15B).

The clinician next reduces spinal rod 200 into seat 110 of screw housing 100. Often times there may be 15 mm or more of travel required in order to reduce spinal rod 200 fully within the seat 110 of screw housing 100 such that spinal rod 200 and screw housing 100 can be locked. Manually rotating shaft 50, 50a such a distance can be cumbersome, tedious, and time consuming. The second position of button 60, 1600 of rod reducer apparatus 10, 1000 permits the clinician to perform course adjustments and quickly slide shaft 50, 50a distally to position anvil 40 against spinal rod 200 to effect a reduction of spinal rod 200 into screw housing 100. With button 60, 1600 of rod reducer apparatus 10, 1000 in the second position, shaft 50, 50a is uncoupled from a threaded portion 66, 1604 of rod reducer apparatus 10, 1000, allowing shaft 50, 50a to freely slid distally through the opening 26, 1202 of the housing 20, 1200. Free translation of shaft 50, 50a permits anvil 40 to rapidly move distally in relation to housing 20, 1200 towards and into abutment with spinal rod 200. In the envisioned method of reducing a spinal rod, with button 60, 1600 in the second position, the clinician freely slides shaft 50, 50a through the opening 26, 1202 of housing 20, 1200 until anvil 40 abuts spinal rod 200. The clinician continues to slide shaft 50, 50a, and anvil 40 attached thereto, distally causing spinal rod 200 into near abutment with screw housing 100. With a plurality of rod reducer apparatus 10, 1000, where each rod reducer apparatus 10, 1000 is mounted to a different bone screw "BS", the clinician is able to gradually reduce the spinal rod 200 to a plurality of bone screws "BS" by sequentially reducing each rod reducer apparatus 10, 1000 all or part way until all rod reducer apparatus 10, 1000 have been actuated fully and the spinal rod 200 is reduced into all of the adjacent bone screws "BS".

Once the anvil 40 is in abutment to spinal rod 200, and/or spinal rod 200 is in abutment to screw housing 100, the clinician may move button 60 into the first position or allow button 1600 to transition to the first position. In the first position, shaft 50 is coupled to the threaded portion 66 of the elongated throughhole 64 of the button 60 such that the clinician may make fine adjustments and manually, or with a surgical tool (not shown), rotate shaft 50 causing anvil 40 to drive spinal rod 200 into securement with screw housing 100. Similarly, with regards to rod reducer apparatus 1000, in the first position, shaft 50a is coupled to the threaded portion 1604 of the button 1600 such that the clinician may make fine adjustments and manually, or with a surgical tool (not shown), rotate shaft 50a causing anvil 40 to drive spinal rod 200 in secure engagement with screw housing 100. In the first position of either button 60 or button 1600, the clinician is provided a mechanical advantage of torque driven rotation of shaft 50, 50a.

With the rod reducer apparatus 10, 1000 attached to bone screw "BS", it is further envisioned that the clinician may additionally use rod reducer apparatus 10, 1000 to further assist the alignment of spinal rod 200 between multiple bone screws "BS". The clinician is provided a mechanical advantage to further bend or shape spinal rod 200 while spinal rod 200 is securely held by both rod reducer apparatus 10, 1000 and the screw housing 100 of the bone screw "BS". In this configuration, the clinician may make final adjustments to the spinal rod 200 when connecting spinal rod 200 between multiple bone screws "BS". After spinal rod 200 is properly aligned, the clinician may further reduce spinal rod 200 to secure the spinal rod 200 into the screw housing 100 of the bone screw "BS".

Upon final alignment of spinal rod 200 between multiple bone screws "BS", and/or securement of spinal rod 200 into screw housing 100, the clinician may place button 60 into the second position or allow button 1600 to transition to the second position. In the second position, shaft 50, 50a can again slide freely within the opening 26, 1202 of the housing 20, 1200 to permit anvil 40 to quickly and easily move proximally with respect to housing 20, 1200. Once the clinician moves shaft 50, 50a and anvil 40 into a proximal most position (as seen in FIGS. 1, 9A, and 15A), arm members 30 of rod reducer apparatus 10, 1000 may be decoupled from the screw housing 100, permitting the clinician to detach rod reducer apparatus 10, 1000 from the bone screw "BS".

In accordance with the present disclosure, it is envisioned that the clinician may perform the method described above with multiple bone screws "BS", implanted in sequence to a number of vertebrae, to facilitate the reduction of spinal rod 200 into and between multiple screw housings 100. It is envisioned that the clinician may be provided with multiple spinal rods 200. The clinician may perform the method described above to facilitate the reduction of multiple spinal rods 200 into multiple screw housings 100 to a number of vertebrae in sequence. It is further envisioned that the clinician may be provided with multiple bone screws and spinal rods of varying sizes.

In accordance with the present disclosure, a kit will be described with reference to FIGS. 1-15B. The kit includes a rod reducer apparatus 10, 1000 in a package (not shown). The kit may further include a bone screw "BS", a spinal rod 200, an orthopedic tool or device (not shown), and instructions for use. Examples of the orthopedic tool or device may be a tightening or loosening tool, an alignment tube, or a locking device. It is further envisioned, that the kit may include multiple rod reducer apparatus 10, 1000, multiple bone screws "BS", and multiple spinal rods 200. Further, the kit may include a variety of sizes of bone screws "BS" and spinal rods 200. The package may include a thermoformed plastic tray and/or other packaging materials within the view of those skilled in the art.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the claims of the present application and their legal equivalents, rather than by the examples given.

What is claimed is:

1. A rod reducer apparatus comprising:
    a housing having an opening and defining a longitudinal axis;
    a shaft disposed through the opening, the shaft having threads formed thereon;
    an anvil coupled to the shaft;
    a button slidably coupled to the housing and transitionable between a first position wherein the threads of the shaft are engaged with threads on the button and a second position wherein the threads of the shaft are spaced apart from the threads on the button, the button biased towards the first position, the button slidable between the first and second positions along a first axis that defines an acute angle with respect to the longitudinal axis; and
    first and second arm members operatively coupled to the housing and configured to engage a bone screw, wherein rotation of the shaft with the button in the first position translates into linear movement of the shaft relative to the housing and linear movement of the shaft with the button in the second position is independent of shaft rotation.

2. The rod reducer apparatus of claim 1, further comprising a spring element for biasing the button towards the first position.

3. The rod reducer apparatus of claim 2, wherein the shaft cooperatively engages threads of the button with the button in the first position.

4. The rod reducer apparatus of claim 2, wherein the first and second arm members are pivotably coupled to the housing.

5. The rod reducer apparatus of claim 2, wherein the first and second arm members are flexibly coupled to the housing.

6. The rod reducer apparatus of claim 2, wherein a first surface of the button includes the threads.

7. The rod reducer apparatus of claim 6, wherein the first surface of the button transitions away from the longitudinal axis of the housing when in the second position.

8. The rod reducer apparatus of claim 6, wherein the first surface of the button is defined on an outer surface thereof.

9. The rod reducer apparatus of claim 2, wherein the button has an ergonomic grip feature disposed on a second surface.

10. The rod reducer apparatus of claim 1, wherein the first and second arms are repositionable towards a parallel configuration as the anvil is moved away from the housing.

11. The rod reducer apparatus of claim 1, further comprising a receiving saddle disposed on the anvil, such that the receiving saddle cooperatively engages with a surface of a spinal rod.

12. The rod reduction apparatus of claim 11, wherein the receiving saddle is generally formed into an arch, and is adapted to engage a variety of spinal rod diameters.

13. A method of reducing a spinal rod into a bone screw comprising:
    providing a rod reducer apparatus including:
        a housing having an opening and defining a longitudinal axis;
        a shaft disposed through the opening, the shaft having threads formed thereon;
        an anvil coupled to the shaft;
        a button slidably coupled to the housing and transitionable between a first position wherein the threads of the shaft are engaged with threads on a first surface of the button and a second position wherein the threads of the shaft are spaced apart from the first surface, the button slidable between the first and second positions along a first axis that defines an acute angle with respect to the longitudinal axis; and
        first and second arm members operatively coupled to the housing and configured to engage a bone screw, the first and second arms movable towards a parallel configuration as the anvil is advanced away from the housing,
        wherein rotation of the shaft with the button in the first position translates into linear movement of the shaft relative to the housing and linear movement of the shaft with the button in the second position is independent of shaft rotation;
    coupling the rod reducer apparatus with the bone screw;
    positioning the spinal rod between the anvil and the screw housing of the bone screw;
    transitioning the button of the rod reducer apparatus into the second position;
    sliding the shaft distally such that the first and second arm members grasp the bone screw; and
    engaging the spinal rod with the anvil.

14. The method of claim 13, further comprising:
    transitioning the button of the rod reducer apparatus to the first position; and
    rotating the shaft such that the anvil travels linearly with respect to the housing towards the spinal rod to urge the spinal rod into engagement with the screw housing of the bone screw.

15. The method of claim 14, further comprising transitioning the button of the rod reducer apparatus to the second position and sliding the anvil away from the spinal rod.

16. The method of claim 15, further comprising:
    translating the anvil proximally into a proximal most position; and
    decoupling the first and second arm members of the rod reducer apparatus from the bone screw.

17. The method of claim 13, further comprising:
selecting the spinal rod from a plurality of spinal rods having varying diameters;
selecting the bone screw from a plurality of bone screws having a variety of sizes; and
reducing the selected spinal rod into the selected bone screw.

18. The method of claim 13, further comprising implanting at least one bone screw into a bone of a subject.

* * * * *